United States Patent
Thridandam et al.

(10) Patent No.: US 12,319,637 B2
(45) Date of Patent: Jun. 3, 2025

(54) HIGH PURITY ETHYLENEDIAMINE FOR SEMICONDUCTOR APPLICATIONS

(71) Applicant: VERSUM MATERIALS US, LLC, Allentown, PA (US)

(72) Inventors: Hareesh Thridandam, Carlsbad, CA (US); Stuart H. Dimock, Lake Forest, CA (US); Steven Gerard Mayorga, Oceanside, CA (US); Ronald Martin Pearlstein, San Marcos, CA (US)

(73) Assignee: Versum Materials US, LLC, Tempe, AZ (US)

( * ) Notice: Subject to any disclaimer, the term of this patent is extended or adjusted under 35 U.S.C. 154(b) by 252 days.

(21) Appl. No.: 17/362,989

(22) Filed: Jun. 30, 2021

(65) Prior Publication Data

US 2021/0323907 A1  Oct. 21, 2021

Related U.S. Application Data

(62) Division of application No. 15/649,271, filed on Jul. 13, 2017, now abandoned.

(60) Provisional application No. 62/364,959, filed on Jul. 21, 2016.

(51) Int. Cl.
| | | |
|---|---|---|
| *C07C 211/10* | (2006.01) | |
| *B01J 20/18* | (2006.01) | |
| *B01J 20/28* | (2006.01) | |
| *B08B 9/08* | (2006.01) | |
| *B65D 81/20* | (2006.01) | |
| *C07C 209/84* | (2006.01) | |
| *C07C 209/86* | (2006.01) | |
| *H01L 21/67* | (2006.01) | |

(52) U.S. Cl.
CPC ............ *C07C 211/10* (2013.01); *B01J 20/18* (2013.01); *B01J 20/2808* (2013.01); *B08B 9/08* (2013.01); *B65D 81/20* (2013.01); *C07C 209/84* (2013.01); *C07C 209/86* (2013.01); *H01L 21/67017* (2013.01)

(58) Field of Classification Search
CPC ... C07C 211/10; C07C 209/84; C07C 209/86; B01J 20/18; B01J 20/2808; B08B 9/08; B65D 81/20; H01L 21/67017
USPC ........................................................ 564/498
See application file for complete search history.

(56) References Cited

U.S. PATENT DOCUMENTS

| | | |
|---|---|---|
| 3,394,186 A | 7/1968 | Muhlbauer |
| 4,273,621 A | 6/1981 | Fornoff |
| 8,664,446 B1 | 3/2014 | Besancon et al. |
| 2006/0272501 A1 | 12/2006 | Plee et al. |
| 2010/0087684 A1 | 4/2010 | Do et al. |
| 2016/0020091 A1 | 1/2016 | Saly et al. |
| 2016/0024647 A1 | 1/2016 | Saly et al. |
| 2016/0035542 A1 | 2/2016 | Hausmann |
| 2016/0060754 A1 | 3/2016 | Noh et al. |

FOREIGN PATENT DOCUMENTS

| | | |
|---|---|---|
| CN | 101407466 A | 4/2009 |
| CN | 105585504 A | 5/2016 |
| DE | 1955827 A1 | 5/1971 |
| JP | 7278064 A | 10/1995 |
| JP | 2013241389 A | 12/2013 |
| WO | 2018017830 A | 1/2018 |

OTHER PUBLICATIONS

Creamer, R. M., et al., "Anhydrous Ethylenediamine", Technical Note, p. 162.
Mukherjee, L. M., et al., "Preparation of Anhydrous Ethylenediamine", A Report Prepared for the International Union of Pure and Applied Chemistry by the Commission of Electroanalytical Chemistry, pp. 421-426.
"Ethyleneamines storage and handling," Dow Chemical Company, Nov. 2001, pp. 7 and 9.

*Primary Examiner* — Ana Z Muresan
(74) *Attorney, Agent, or Firm* — Daniel Roth; Versum Materials US, LLC

(57) ABSTRACT

A method for making the EDA that is suitable for use in thin-film semiconductor processing applications, are disclosed. The EDA is purified to remove water and trace metals. Water levels below about 50 ppm by weight are achieved by passing liquid through 3A type molecular sieve in a packed bed. Metallic impurities are removed by distillation and the resulting product is packaged in specially dried and optionally pre-conditioned containers.

11 Claims, No Drawings

HIGH PURITY ETHYLENEDIAMINE FOR SEMICONDUCTOR APPLICATIONS

CROSS-REFERENCE TO RELATED APPLICATIONS

This Application is a Divisional of application Ser. No. 15/649,271, filed Jul. 13, 2017. Application Ser. No. 15/649,271 claims the benefit of Provisional Application No. 62/364,959, filed on Jul. 21, 2016. The disclosure of both Applications (No. 62/364,959 and Ser. No. 15/649,271) are hereby incorporated by reference.

BACKGROUND OF THE INVENTION

Ethylenediamine (EDA) is commonly used in the chemical industry. New applications for this chemical in semiconductor processing are being developed (for instance, see US2016060754A, US2016020091A, US2016024647A, US2016035542A, and US2017114459A) however, where the chemical must be delivered to the process without carrying metallic impurities or oxygen containing impurities such as water which could adversely affect the quality of the thin films grown or processed with this reagent. EDA forms adducts (1:1 and 1:2) with water, making it difficult to dry. One complexity is that it forms a high-boiling azeotrope containing about 15% water by weight, making dehydration by conventional fractional distillation impossible. Also it is a very potent chelator of many metallic elements such as iron, sodium, nickel, aluminum and the like. This property makes it difficult to transport or contain this chemical with the metallic components conventionally used with semiconductor chemicals without the risk of imparting significant contamination.

Ethylenediamine (EDA) is most commonly is synthesized in the presence of water. This water must be removed for many applications. Since it forms a high-boiling azeotrope with water, EDA cannot be dried by conventional fractional distillation alone. The use of benzene or other water entrainers to break the azeotrope has be successfully employed. For example, Creamer and Chambers (doi:10.1149/1.2781223 *J. Electrochem. Soc.* 1954, 101(3), 162) are able to bring water content to below 0.5% (5000 ppm by weight) and reduce the conductivity to below $10^{-5}$ $ohm^{-1}$ $cm^{-1}$ with a number of water entrainers, preferably benzene.

In U.S. Pat. No. 3,394,186, Muhlbauer describes a method for the production of substantially anhydrous ethylenediamine comprising the steps of (A) contacting ethylene dichloride with a molar excess of ammonia in aqueous solution at a temperature within the range of about 75° C. to about 175° C. to provide a crude reaction mixture containing ethylenediamine dihydrochloride, (B) contacting said crude reaction solution with about 50 to about 75 wt. percent aqueous solution of caustic in a combination neutralization distillation zone at a temperature of about 80° C. to about 100° C. to neutralize said ethylenediamine dihydrochloride and flash a water and amine azeotrope overhead, (C) contacting said azeotrope in liquid solution with from about 0.5 to about 1.5 parts per part of azeotrope of a 60 to 80 wt. percent aqueous solution of caustic to selectively, partially remove water from said azeotrope and (D) fractionating said partially dewatered azeotrope at a subatmospheric pressure of about 100 to 500 mm of mercury absolute to obtain an anhydrous distillate ethylenediamine product.

In German Patent No 1,955,827A (1971), Adam and Merkel teach that ethylenediamine can be dehydrated by distillation with piperidine. Thus, 500 parts 80% EDA soln. in water and 280 parts piperidine were distd. at 1 atm. and 2:1 reflux ratio in a column of 20 theoretical plates to give 371 parts EDA with <0.1% $H_2O$ content.

All of these methods make a product which has too high residual water content and other impurity species (such as the entraining agent) making it unsuitable for use in semiconductor processing. Also, the requirement of recycling the entraining agent and complex integration scheme with recycle streams makes such processes undesired for specialty chemical manufacturing.

The use of chemical drying agents to make nominally anhydrous EDA have been disclosed. Mukherjee and Bruckenstein, in a report for the International Union of Pure and Applied Chemistry on the Preparation of Anhydrous Ethylenediamine (*Pure Appl. Chem.* 1966, 13, 421) recommend a multi-step procedure starting with a) Pre-drying by shaking 98% EDA with 5A molecular sieves for 12 h and then decanting followed by b) Shaking with a mixture of calcium oxide and potassium hydroxide for 12 h followed by c) fractional distillation from freshly activated 5A molecular sieve with a 1:20 reflux ratio and d) a second distillation from metallic sodium under nitrogen. This process yields EDA having water content ~0.015 mole/L (0.27 g/L or about 300 ppm by weight).

Even when EDA is distilled to remove metallic impurities, it can dissolve many metals when exposed to surfaces containing metal oxides. While not wishing to be bound by theory, it is believed that the metal oxides or metal hydroxides are dissolving to form soluble EDA complexes. It is further believed that this process is accelerated and enhanced by the presence of water, either free water or water complexed with EDA or water adsorbed upon an interior surface of a metal container housing the EDA. Furthermore, the presence of halide, especially chloride, in the EDA can increase the dissolution of metals by promoting corrosion and increase the concentration of metal-EDA complexes.

Other conventional methods for treating EDA are disclosed by Mukherjee in *Pure Appl. Chem.* 1966, 13, 421; U.S. Pat. No. 4,273,621 A and JP7278064A.

The disclosure of the previously identified publications, patents and patent applications is hereby incorporated by reference.

BRIEF SUMMARY OF THE INVENTION

The instant invention solves problems associated with conventional methods and provides improved ethylenediamine (EDA) compositions, and methods for processing the EDA and to methods for treating containers that store the EDA in order to provide EDA which is suitable for use in thin-film semiconductor processing applications. Using the inventive processes for removing water (and water moieties) from EDA and storing the inventive EDA in a dried and pretreated container, reduces the corrosion rate of the container and in turn permits storing the EDA for relatively long periods of time while maintaining a defined purity.

In one aspect of the invention, EDA is purified to remove water and trace metals. Water levels below about 50 ppm by weight are achieved by passing liquid through 3A type molecular sieve (zeolite) in a packed bed. Metallic impurities are removed by distillation and the resulting product is packaged in specially dried and, typically, in pre-conditioned containers.

For semiconductor applications, low metal elemental impurities are needed to avoid electrical failures of devices.

The instant invention also provides a container that has been pre-treated in a manner that reduces water and metal elements leaching from the container into the EDA.

Another aspect of this invention is the absence of substantial quantities of metallic sodium needed during the distillation. Sodium metal is highly flammable and air sensitive and can potentially add undesired sodium contamination to the product.

The aspects of this invention can be used alone or in various combinations with each other.

DETAILED DESCRIPTION OF THE INVENTION

The inventive EDA composition is about 99 to about 99.99, about 99.8 to about 99.95 and typically about 99.8 to about 99.9 weight percent pure EDA and, in some cases, greater than 99.9 weight percent pure The inventive EDA contains less than about 50 ppm water, typically less than about 20 ppm water and in most cases less than about 10 ppm water, or 5 ppm water or 1 ppm water, to non-detectable water levels when measured by gas chromatography with discharge ionization detection. The inventive EDA contains less than about 100 ppb each of the following trace metals: aluminum, chromium, copper, iron, magnesium, manganese, molybdenum, nickel, titanium, and zinc. In particular, the inventive EDA contains less than about 20 ppb, typically less than about 10 ppb and in most cases less than about 1 ppb each of trace metals down to non-detectable levels by inductively coupled plasma mass spectrometry (ICP/MS). The inventive composition is analyzed by GC/TCD or GC/PDID to confirm the amounts of EDA and water and by ICP/MS for trace metals. The inventive EDA composition may also contain less than about 10 ppm, typically less than about 5 ppm and in most cases less than about 1 ppm halides and in particular chlorine. The inventive EDA composition may be analyzed for halide content (specifically chloride ion) by ion chromatography of an aqueous solution. The inventive EDA composition may also contain less than 100 ppb each, less than 50 ppb each, less than 20 ppb each, less than 10 ppb each, less than 1 ppb each, and in most cases less than 0.5 ppb each of alkali metals, (such as sodium, potassium, magnesium, calcium), aluminum, and stainless steel elements and in particular aluminum, chromium, iron, molybdenum, and nickel. The inventive EDA composition may be analyzed for alkali metal, aluminum and stainless steel element content (specifically sodium, aluminum, chromium, iron, manganese, molybdenum, and nickel) by ICP/MS.

The inventive EDA can be stored in any container or delivery system suitable for supplying the EDA to a semiconductor manufacturing system. Examples of suitable containers and delivery systems are disclosed in U.S. Pat. Nos. 7,334,595; 6,077,356; US5,06,9244; U.S. Pat. No. 5,465, 766 the disclosure of which is hereby incorporated by reference. The container can comprise either glass (borosilicate or quartz glass) or type 316, 316L, 304 or 304L stainless steel alloys (UNS designation S31600, S31603, S30400 S30403).

Prior to introducing the inventive EDA into the container, the container and or the delivery system is pre-treated by 1) drying by either flowing dry inert gas (such as dry air, dry nitrogen, dry helium or dry argon gas or combination thereof) or by application of vacuum periodically for a period of time to achieve a pressure below about 1 Pa to about 10 kPa (or a combination of the two processes) wherein drying is facilitated by applying heat to the dry inert gas or the container or both from about 60° C. to about 210° C.; then 2) filling the pre-dried system with purified EDA (e.g., the inventive EDA), and allowing the surfaces to be exposed to the liquid for a period ranging from about 1 hour to about 1 week to remove any remaining absorbed water molecules on the inner surface of the container. In one embodiment, the container can also be filled with water soluble solvents such as tetrahydrofuran (THF), acetonitrile, or other organic amines to help remove absorbed water molecules on the inner surface of the container before step 1 or 2 above.

A preferred method involves heating the system to about 180° C. for about 24 h while maintaining pressure below 10 Pa. The container is filled to the maximum safe fill level with EDA prepared according to this invention and stored at about 23° C. for about 48 h before removing the liquid and refilling with the desired quantity of high purity EDA (e.g., the inventive EDA).

The inventive purity ethylenediamine is prepared by a process comprising two-steps. The first step of the process comprises passing commercially available ethylenediamine as a liquid through a packed bed comprising a molecular sieve and collecting this material in a container. While any molecular sieve that preferentially removes water relative to EDA can be employed, preferred molecular sieves comprise 3A molecular sieves (UOP type 3A zeolite, CAS registry 308080-99-1 with approximate formula $K_nNa_{12-n}[(AlO_2)_{12}(SiO_2)_{12}] \cdot xH_2O$) where n ranges from about 6-10, typically about 8. The pressure applied to the EDA when passing the EDA through the sieve ranges from about 1 psi to about 15 psi, and at a temperature that ranges from about 10° C. to about 35° C., in order to achieve an EDA weight hourly space velocity (WHSV) between 0.1 to 10 $h^{-1}$, preferably between 0.2 and 5 $h^{-1}$ and typically between 0.5 to 1 $h^{-1}$. The 3A molecular sieve has a particle size of 4-8 mesh, though a smaller mesh size may be advantageous if larger space velocities are used. The sieve bed should be long enough to contain the mass transfer zone. With 4-8 mesh pellets, a bed length of at least 1 m is preferred when the WHSV is about 0.5. Detection of water breakthrough from this column may be determined by monitoring the conductivity of the liquid exiting the column using a Emerson/Rosemount conductivity analyzer model 1056 with flow cell sensor model 404.

The material so treated by the 3A molecular sieve is then subjected to distillation in order to remove metallic impurities. Distillation can be performed in batch fractional distillation apparatus fitted with either a packed or a sieve tray column and with a reboiler that is externally heated and an overhead condenser. Preferably, the distillation system is constructed of glass with flanges sealed with poly(tetrafluoroethylene) gaskets though other materials, such as stainless steel, may be used if pre-treated according to the methods disclosed herein. Distillation is conducted at overhead pressures ranging from 10 kPa to 110 kPa absolute. The reflux ratios ranging between 60:1 and 1:1 may be employed with reflux rates up to 1 kg/h per $cm^2$ of column cross sectional area. Such a process is capable of producing the inventive EDA (e.g., with less than about 50 ppm water and less than about 100 ppb by weight each of trace metal elements).

The distilled material is stored in dried containers, preferably in electropolished stainless steel vessels that have been pre-treated with dry EDA. The containers are pre-treated by filling with dry EDA and allowing to soak at ambient temperature until such time that the Fe and water concentrations have plateaued (reached an asymptote) and no longer increase significantly over time. A soak time between 1 hour and several weeks is possible, typically about 1 week is required to reach this point. By providing a high purity EDA with reduced water into a dried and pre-treated container, the leach rate of metal from the container is reduced. The high purity of the stored EDA under a headspace of inert gas (such as helium, nitrogen, argon, or any mixture thereof) can be maintained for an extended period of time, thereby enhancing the suitability of the stored EDA for use in semiconductor manufacturing.

The following Examples illustrate certain aspects of the invention and do not limit the scope of the appended claims.

EXAMPLES

Example 1a—Method for Making High Purity EDA

A 2"×40" stainless steel column fitted with stainless steel sanitary flanges and PTFE gaskets was prepared for service by inserting a fine stainless steel screen support then ca. 2" of quartz wool packing followed by a coarse mesh stainless steel screen support. The bottom of the column was then capped with a sanitary flange and gasket. To the column was charged 1.2 kg of 3A molecular sieves (Sigma Aldrich 208574). The column was tapped with a rubber mallet to aid in settling of the material. The top support is prepared by inserting a fine mesh stainless steel screen at the surface of the sieve bed, followed by ca. 2" quartz wool packing then a coarse mesh stainless steel screen. The column was then sealed with a PTFE gasket and sanitary flange.

The molecular sieves were then activated by placing the column under dynamic vacuum of <0.050 Torr and then slowly ramping the heat by 20° C. to 70° C. over 1 h, followed by a 4 hr soak at 70° C., then ramping from 70° C. to 300° C. over 2.5 h followed by a 4 hr soak at 300° C. Heat is applied externally with heating tapes controlled by the use of a digital temperature controller. The column was allowed to cool under dynamic vacuum from 300° C. to 20° C. over 8 hr.

A stainless steel source vessel was filled with 32.68 kg of ethylenediamine (supplied by Dow Chemical Company) and was connected to the nitrogen supply line to pressurize the headspace. The diptube of the container was connected to the bottom inlet of the adsorption column. A 38 L thoroughly-dried electropolished stainless steel receiver vessel was placed on the balance and connected to the column top outlet. The receiver was also connected to a nitrogen-purged vent. The balance under the receiver was then tared to record the mass of material collected.

Collection was initiated by opening in sequence: the nitrogen supply pressure regulated at 12.5+/−0.5 psi to the source material vessel headspace valve, the source material dip tube valve, the bottom valve at the base of the column, the top valve at the top of the column, the needle valve flow control valve, the discharge valve, the receiver head space valve, the receiver vent valve, and the vent system valve. Pressures between 7.5-8.5 psig were recorded at the top of the column. The rate of flow was governed by the needle valve, and was maintained at 650+/−25 g/hr. The water content of the EDA collected in the receiver was <7 ppm by weight.

When the moisture level in the material from the column discharge exceeds the specification for the system, the bed was regenerated. The flow is stopped by closing in sequence: the nitrogen source valve, the source vessel head space valve, the column bottom diverter valve, the column top diverter valve, and the regulating needle valve. The line below the needle valve is then blown dry with nitrogen to remove free liquid. The receiver is then sealed by closing in sequence: The receiver vent valve, the vent connector valve, and the receiver head space valve. The column is then purged dry by applying nitrogen pressure through the column top diverter valve and discharging through the column bottom discharge valve into a column drains receiver. Once all free liquid (approximately 0.6 kg) has been discharged into the column drains receiver, the column drains receiver is then removed and replaced with a solid $CO_2$ cooled trap.

Dynamic vacuum is then applied to the cooled trap eventually resulting in a pressure of <0.050 torr. The molecular sieves are then reactivated by placing the column under dynamic vacuum of <0.050 Torr and then gently ramping the heat applied through the heating tapes by the use of a digital temperature controller. The heater duty cycle is 20° C. to 70° C. over 1 hr. followed by a 4 hr soak at 70° C. to remove adsorbed liquid from the bead surfaces, then a ramp from 70° C. to 300° C. over 2.5 h followed by a 4 hr soak at 300° C. to remove water from the sieve. Upon completion of the soak at 300° C. the column is allowed to cool under vacuum from 300° C. to 20° C. over 8 hr. The column is then be blocked in at the pump and observed for leak tightness using vacuum decay. Once integrity has been confirmed the column is then backfilled with nitrogen rendering it ready for use in dehydration service.

Example 1b—Method for Distillation

15 L of the dried EDA collected in the stainless steel receiver was anaerobically transferred to a 20 liter glass reboiler heated with a 2200 watt, 3 zone heating mantle. The reboiler is connected to a 66-inch long, 2-inch I.D. glass column filled with approximately 5 feet of 0.16-inch stainless steel ProPak distillation packing topped with a glass condenser with coolant coils connected to a 500 Watt chiller and connected to a nitrogen purged atmospheric pressure vent.

Fractional distillation was conducted by applying heat to the reboiler and refluxing for 1 h followed by collection of 500 mL of pre-fraction at 0.4 L/h. A total of 13.8 L of pure EDA were collected in a pre-dried 38 L electropolished stainless steel vessel with surface roughness <0.8 μm $R_a$ at 1.8 L/h. The high purity EDA so produced contained <1 ppb of Fe, Cr, Ni and Mo as measured by inductively coupled plasma mass spectrometry and <10 ppm of water as measured by gas chromatography with thermal conductivity detection. The Cl content measure by ion chromatography was <10 ppm.

Example 2—Method for Treating Container

Electropolished stainless steel containers with <0.8 μm $R_a$ internal surface finish were dried by purging with 4 to 6 L/min of heated, purified nitrogen gas while baking the container in an oven at 110° C. for 8 hours (e.g., electropolished to a surface roughness of about 25 to 40 μin Ra in accordance with U.S. Pat. No. 8,590,705; hereby incorporated by reference). Thus dried, the containers are treated further by filling them with EDA produced in accordance with Example 1. The containers were soaked with dry EDA at ambient temperature and samples of EDA were periodically removed from the container and analyzed for moisture and iron concentrations. Samples collected on a daily basis show an increase in moisture and iron concentrations until they reach an asymptotic value where the concentration no longer increases with time. The leaching rate appears to stabilize with increasing storage time in the unpassivated vessel. At t=0 days, Fe=0.69 ppb. At t=2 days, Fe=1.61 ppb. At t=7 days, Fe=1.22 ppb. The iron leaching rate at 2 days is 0.46 ppb/day and has decreased to 0.08 ppb/day at 7 days. The time to reach the asymptotic value is thus 1 week.

Example 3—Leach Rate for Treated Container

EDA produced in accordance with Example 1 was placed into a container pre-treated in accordance with Example 2. The leach rate of trace metals from the container into the EDA was determined as follows: samples of EDA were periodically collected from the container over the time period of the study. The samples were analyzed for trace metals by inductively coupled mass spectrometry. The leach rate is the slope of the linear fit of the trace metal concentration vs. time over the period of the study. The analytical results of this Example are listed in Table 1. This Example demonstrates that the leach rate of metals from the container can be reduced when the inventive EDA is stored in the inventive pre-treated container.

filling it with the inventive dry EDA containing 17 ppm $H_2O$. After a storage duration of 305 days at ambient temperature, water content increased to 25 ppm, thereby indicating that the vessel surface had less residual moisture than an untreated surface prior to filling. This vessel exhibited a corrosion rate of 0.02 ppb/day Ni. Storage shelf life is thus 50 days at a 1 ppb Ni impurity specification.

Example 7

A 38-L stainless steel vessel was dried to <100 ppb $H_2O$ with an oven dryer wherein the entire vessel is placed within the oven thereby uniformly heating the entire vessel. The internal surfaces were passivated by soaking with the inventive dry EDA for 48 hours, which was then removed prior to filling it with the inventive dry EDA containing 8 ppm $H_2O$. After a storage duration of 330 days at ambient temperature, water content increased to 22 ppm. Without wishing to be bound by any theory or explanation, it is believed that the vessel surface had even less residual moisture than the passivated band dried vessel in Example 3 prior to filling.

TABLE 1

| | Fill in 19-L vessel | Age (days) | $H_2O$ (ppm) (init) | $H_2O$ (ppm) (end) | Al (ppb/day) | Cr (ppb/day) | Cu (ppb/day) | Fe (ppb/day) | Mg (ppb/day) | Mn (ppb/day) | Mo (ppb/day) | Ni (ppb/day) | Ti (ppb/day) | Zn (ppb/day) |
|---|---|---|---|---|---|---|---|---|---|---|---|---|---|---|
| | | | | | | | | Leaching Rate | | | | | | |
| Dry EDA passivation | 4 kg | 140 | 17 | 18 | 0.09 | 0.00 | 0.00 | 0.02 | 0.022 | 3E-04 | 1E-04 | 0.032 | -1.E-03 | 0.014 |
| Dry no passivation | 14.6 kg | 176 | 67.5 | 130 | -1.22 | 0.019 | 0.074 | 0.005 | -0.05 | 0.007 | 0.006 | 0.025 | -0.002 | 0.012 |
| Dry no passivation | 14.6 kg | 244 | 58.8 | 1646 | -0.20 | 0.157 | 0.039 | 0.288 | -0.007 | 0.02 | 0.009 | 0.065 | 0.044 | 0.009 |

Example 4

A 19-L stainless steel vessel was dried at a temperature of 120° C., evacuated, purged with nitrogen gas and cooled to obtain <500 ppb $H_2O$ interior surface moisture. The vessel was heated with band heater placed around an exterior area of the vessel. The internal surfaces were not treated prior to filling with EDA containing 59 ppm $H_2O$. After a storage duration of 244 days at ambient temperature, water content increased to 1646 ppm, suggesting that the vessel surface had residual moisture prior to filling. This vessel exhibited a corrosion rate of 0.288 ppb/day Fe. Storage shelf life is thus 3 days at a 1 ppb Fe impurity specification.

Example 5

A 19-L stainless steel vessel was dried to <500 ppb $H_2O$ with the band heater in accordance with Example 4. The internal surfaces were not treated prior to filling with EDA containing 68 ppm $H_2O$. After a storage duration of 176 days at ambient temperature, water content increased to 130 ppm, thereby indicating that the vessel surface had residual moisture prior to filling. This vessel exhibited a corrosion rate of 0.025 ppb/day Ni. Storage shelf life is thus 40 days at a 1 ppb Ni impurity specification.

Example 6

A 19-L stainless steel vessel was dried to <500 ppb $H_2O$ with the band heater in accordance with Example 4. The internal surfaces were passivated by soaking with the inventive dry EDA for 48 hours, which was then removed prior to This vessel exhibited a corrosion rate of 0.00043 ppb/day Ni. Storage shelf life is thus 2300 days at a 1 ppb Ni impurity specification.

The leach rate was determined in accordance with Example 3. Detailed analytical results of Examples 4-7 are listed in Table 2.

TABLE 2

Stainless Steel Corrosion Rates as a Function of EDA Moisture Content and Vessel Surface Treatment

| | Corrosion Rates (ppb/day) | | | |
|---|---|---|---|---|
| | Ex 4 | Ex 5 | Ex 6 | Ex 7 |
| Vessel Size (L) | 19 | 19 | 19 | 38 |
| Vessel Drying Method | Band heater (<500 ppb moisture) | Band heater (<500 ppb moisture) | Band heater (<500 ppb moisture) | oven dry (<100 ppb moisture) |
| Vessel Surface Treatment | none | none | EDA passivation | EDA passivation |
| Initial $H_2O$ (ppm) | 59 | 68 | 17 | 8 |
| Final $H_2O$ (ppm) | 1646 | 130 | 25 | 22 |
| Duration (days) | 244 | 176 | 305 | 330 |
| Cr (ppb/day) | 0.157 | 0.019 | 0.004 | 0.00045 |
| Fe (ppb/day) | 0.288 | 0 | 0.002 | -0.0013 |
| Mn (ppb/day) | 0.02 | 0.007 | 0.001 | 0.00013 |
| Mo (ppb/day) | 0.009 | 0.006 | 0 | 0.00020 |
| Ni (ppb/day) | 0.065 | 0.025 | 0.02 | 0.00043 |
| Cu (ppb/day) | 0.039 | 0.074 | 0 | 0.00018 |

TABLE 2-continued

Stainless Steel Corrosion Rates as a Function of EDA Moisture Content and Vessel Surface Treatment

| | Corrosion Rates (ppb/day) | | | |
|---|---|---|---|---|
| | Ex 4 | Ex 5 | Ex 6 | Ex 7 |
| Ti (ppb/day) | 0.044 | 0 | 0 | 0.00023 |
| Zn (ppb/day) | 0.009 | 0.012 | 0 | 0.00050 |

A comparison of Example 4 and 5 illustrates that variability in the effectiveness in drying the vessel can affect the amount of surface water adsorbed which affects the amount of water released into the EDA and in turn the corrosion rate of the vessel (as measured by metal leach rate).

A comparison of Examples 4 and 5 to Examples 6 and 7 illustrates that introducing EDA treated in accordance with Example 1a into a vessel that has been dried and pretreated, achieves a reduced corrosion rate (as measured by metal leach rate). Corrosion rates are reduced by removing water from the EDA as well as adsorbed surface water within the container. Reduced corrosion rates in turn impart improved stability or shelf life to the EDA within the container.

A comparison of Example 6 to Example 7 illustrates that uniform vessel drying (that can be achieved by an oven) further reduces the amount of adsorbed surface water thereby reducing corrosion and increasing shelf life of the EDA.

Comparative Example

This Example compares the method for contacting EDA with a molecular sieve. A five gallon plastic carboy filled with ethylenediamine was treated with activated 3A molecular sieves so that the solid pellets covered the bottom 1-2 inches of the container. The container was swirled to mix and then stored in a dry enclosure and sampled periodically. The moisture content of the liquid was determined over the course of several weeks with the following results, with moisture level measured in ppm by using GC/TCD are listed in Table 3. The process time (for the static contact process in this example) to reach less than 10 ppm moisture is not practical for high volume production.

TABLE 3

Moisture in EDA versus Static Contact Time

| Date | Elapsed | Moisture |
|---|---|---|
| Aug. 18, 2015 | | |
| Aug. 19, 2015 | 1 | 491.8 |
| Aug. 24, 2015 | 6 | 204.6 |
| Sep. 1, 2015 | 14 | 34.4 |
| Sep. 8, 2015 | 21 | 11.4 |

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for treating an ethylenediamine composition comprising:
   contacting the ethylenediamine composition with a molecular sieve comprising type 3A zeolite under conditions sufficient to reduce the amount of water in the ethylenediamine composition to greater than 1 ppm and less than about 50 ppm;
   distilling the ethylenediamine composition under conditions sufficient to reduce an amount of each of aluminum, chromium, copper, iron, magnesium, manganese, molybdenum, nickel, titanium, and zinc to less than about 100 ppb, and
   recovering an ethylenediamine product that is greater than about 99.9 weight percent pure;
   wherein the contacting is carried out by passing the ethylenediamine composition in a liquid through a packed bed comprising the molecular sieve.

2. The method of claim 1, wherein the ethylenediamine product contains less than about 50 ppb each of aluminum, chromium, copper, iron, magnesium, manganese, molybdenum, nickel, titanium and zinc.

3. The method of claim 1, wherein the ethylenediamine product contains less than about 10 ppm of water.

4. The method of claim 1, wherein the ethylenediamine product contains less than about 5 ppm of water.

5. The method of claim 1, wherein the ethylenediamine product contains less than about 5 ppm of halides.

6. The method of claim 1, wherein the halide is chlorine.

7. The method of claim 1, wherein the ethylenediamine product contains less than about 5 ppb of alkali metals.

8. The method of claim 1, wherein the alkali metal is sodium.

9. The method of claim 1, wherein the contacting comprises passing the ethylenediamine composition through a bed of the molecular sieve at a pressure that ranges from 1~15 psi and at a temperature that ranges from 10~35° C.

10. The method of claim 1, wherein contacting the ethylenediamine composition with a molecular sieve takes place at a weight hourly space velocity (WHSV) of 0.1 to 10 $h^{-1}$.

11. The method of claim 10, wherein contacting the ethylenediamine composition with a molecular sieve takes place at a weight hourly space velocity (WHSV) of 0.2 to 5 $h^{-1}$.

* * * * *